United States Patent
Duncan et al.

(10) Patent No.: US 6,537,570 B1
(45) Date of Patent: Mar. 25, 2003

(54) METHOD OF BIOLOGICAL CONTROL

(75) Inventors: Kelvin Winston Duncan, 27b Lodge Place, Christchurch (NZ); Angus Ian Macrae, Christchurch (NZ)

(73) Assignee: Kelvin Winston Duncan, Christchurch (NZ)

( * ) Notice: Subject to any disclaimer, the term of this patent is extended or adjusted under 35 U.S.C. 154(b) by 0 days.

(21) Appl. No.: 09/319,556

(22) PCT Filed: Dec. 9, 1997

(86) PCT No.: PCT/NZ97/00165

§ 371 (c)(1),
(2), (4) Date: Jun. 8, 1999

(87) PCT Pub. No.: WO98/25471

PCT Pub. Date: Jun. 18, 1998

(30) Foreign Application Priority Data

Dec. 9, 1996 (NZ) ................................................ 299903
Jan. 31, 1997 (NZ) ................................................ 314171

(51) Int. Cl.[7] ............................ A61K 9/70; A61K 35/80
(52) U.S. Cl. .................................. 424/443; 424/195.17
(58) Field of Search ............................ 424/443, 195.17

(56) References Cited

U.S. PATENT DOCUMENTS

| | | | |
|---|---|---|---|
| 4,886,756 A | 12/1989 | Kawamura et al. | |
| 5,585,365 A | 12/1996 | Hayashi et al. | |

FOREIGN PATENT DOCUMENTS

| | | |
|---|---|---|
| CN | 1102069 A | 5/1995 |
| CN | 1105566 A | 7/1995 |
| DE | 19646324 A1 | 5/1997 |
| EP | 619112 A1 | 10/1994 |
| EP | 629397 A1 | 12/1994 |
| FR | 2609246 A | 7/1988 |
| JP | 57-36981 | 2/1982 |
| JP | 087294 | 3/1984 |
| JP | 63-63391 | 3/1988 |
| JP | 107549 | 11/1996 |

OTHER PUBLICATIONS

Mitsuo Takano, Jun–Ichi Sado, Takahira Ogawa, Gyozo Terui, "Freezing and Freeze–Drying of *Spirulina platensis*", MicroBiology, 1973, p. 440–444, vol. 10, Academic Press Inc.

Jorjani, G.H.; Amirani, Parvin, "Antibacterial activities of *Spirulina platensis*", Maj. Ilmy Puzshky Danishkadah Jundi Shapur, 1978, 169142n, vol. 91. (Coll. Med. Technol., Jundi Shapur Univ., Ahvaz, Iran).

Nicolas G. Popovich, "Spirulina", *American Pharmacy*, Jun. 1982, p. 8–10, vol. NS22, No. 6.

Orio Ciferri, Orsola Tiboni, "The Biochemistry and Industrial Potential of *Spirulina*", *Annual Review of MicroBiology*, 1985, p. 503–526, vol. 39, No. 15.

Suresh P. Thacker, Raman M. Kothari, V. Ramamurthy, "Obtaining Axenic Cultures of Filamentous Cyanobacterium *Spirulina*", *Biotechniques*, 1994, p. 216–217, vol. 16, No. 2.

Kyoko Hayashi, Toshimitsu Hayashi, Ichiro Kojima, "A Natural Suflated Polysaccharide, Calcium Spirulan, Isolated from *Spirulina platensis*: In Vitro and ex Vitro Evaluation of Anti–Herpes Simplex Virus and Anti–Human Immunodeficiency Virus Activities", *AIDS Research and Human Retroviruses*, 1996, p. 1463–1471, vol. 12.

Toshimitsu Hayashi, Koyoko Hayashi, Masaakira Maeda, Ichiro Kojima, "Calcium Spirulan, and Inhibitor of Enveloped Virus Replication, from a Blue–Green Alga *Spirulina platensis*", *Journal of Natural Products*, 1996, p. 83–87, vol. 59.

*Primary Examiner*—Jose' G. Dees
*Assistant Examiner*—Michael A. Williamson
(74) *Attorney, Agent, or Firm*—Greer, Burns & Crain, Ltd.

(57) ABSTRACT

A method of preparation of a treated Spirulina compound includes the steps of rehydrating desiccated Spirulina, stressing the culture and freeze drying to a powder. The resultant compound has activity as an anti-viral compound and an anti-bacterial compound. It is capable of effecting repair of skin defects in mammals and acting as a preventative agent to skin defects.

15 Claims, No Drawings

METHOD OF BIOLOGICAL CONTROL

TECHNICAL FIELD

The present invention relates to the use of a treated Spirulina compound as a biological agent for the control, prevention and eradication of infections and skin defects in vertebrates and mammals. The present invention also relates to a method of reducing, or avoiding the formation of, skin defects in vertebrates, and particularly mammals.

BACKGROUND ART

The use of Spirulina or Spirulina extracts for care of skin and to improve the appearance of healthy skin is known. Examples of such can be found in EP 629397, FR 2609246, CN 1102069(Abstract), CN 1105566 (Abstract) amongst others. The application of Spirulina or Spirulina extracts to hair or in a shampoo is also known, for example EP 619112.

Spirulina also been found to have anti-viral abilities, as can be seen in U.S. Pat. No. 5,585,365 (Hayashi et al.) A hot water extract of Spirulina from which a calcium polysaccharide was purified was disclosed. The purified extract was effective for the treatment of viral diseases.

In addition Spirulina has been reported as having biological activity for example: to lower blood sugar levels (in diabetes); to lower blood cholesterol; and other effects (Hayashi et al). Other biological activity for Spirulina has been disclosed, for example: by Amirani (Chemical Abstracts, 91:169142n). This disclosure is to the anti-bacterial activity for Spirulina. In U.S. Pat. No 4,886,756 Kawamura discloses a restriction endonuclease from Spirulina. In J 6303391 (Abstract) a method is disclosed for producing a physiologically active substance from Spirulina.

However, in each of the above described types of biological activity of Spirulina, there is no consistency in the method of production of the Spirulina or Spirulina extract. Across the disclosures there is no reference as to whether a particular type of extract or compound produces a particular type of biological activity best.

It is an object of the present invention to overcome this absence by the use of a treated Spirulina compound. It is a further object of one aspect of the present invention to provide an improved method of biological control whereby the vigor of the agent can be controlled by the exclusion of visible light.

Another object of the present invention is the provision of a method of producing a biologically active, treated Spirulina compound which can be used effectively for any of the above described biological activity. A further object of the invention is the provision of a cost effective method as a useful choice to those presently existing.

SCOPE OF THE INVENTION

The present invention provides a method of preparation of a treated Spirulina compound, said method comprising the steps of:
rehydrating desiccated Spirulina cells in a rehydrating solution containing
sodium bicarbonate for between 1 to 12 hours; stressing the culture by one of nutrient diminution or partial desiccation; and
freeze drying the compound.
Preferably the freeze drying produces an axenic compound.

The present invention also provides a method of biological control to inhibit and suppress the growth and effects of biological contaminants by the use of a treated Spirulina compound, said method comprising the steps of: preparing said treated Spirulina compound by the method described above, and
the application of said treated Spirulina compound on or adjacent a target site, said site being selected from the group consisting of:
an external result of the operation of the biological contaminant on a vertebrate, wherein said external result is selected from the group consisting of a papule, a stomatitis, a blister, a lesion, a pustule and a combination thereof; and old target sites where scar tissue remains.

The present invention further provides a method for the repair of skin defects in mammals; said method including the steps of: preparing said treated Spirulina compound by the method described above; and distributing said compound over a target site containing a skin defect; wherein said skin defect is selected from the group consisting of: scars, pits, reddened areas, cracks, burns, blisters, psoriasis, eczema, scaling, wrinkles and a combination thereof.

The present invention further provides a method for the avoidance of skin defects in mammals; said method including the steps of: preparing said treated Spirulina compound by the method described above; and distributing the compound over a target site which could become a skin defect; wherein said skin defect is selected from the group consisting of: scars, pits, reddened areas, cracks, burns, blisters, psoriasis, eczema, scaling, wrinkles and a combination thereof.

Preferably, the method further includes a means to control the vigor of said agent, the means being visible light, and wherein the agent is applied as a liquid culture spray.

Preferably, said compound is a liquid culture and is applied as a spray on or adjacent the target site. Alternatively, said compound is a powder of desiccated cells, evenly distributed over the target site by shake or puffer application in respect of an unicellular or multicellular organism and/or mixing in respect of a growth substrate. Optionally, said compound (liquid culture or powder form) is carried in a base such as a gel or cream for topical application to either an epidermal lesion of a human or animal, or impregnated in a surgical dressing.

BEST MODE FOR CARRYING OUT THE INVENTION

By way of example only, preferred embodiments of the present invention are described in detail, with reference to a series of Examples.

In the description of the preferred embodiments, the terms "fungal contaminants", "companion organisms" and "biological agent" have the meanings given below:
Fungal contaminants—Deuteromycota and Ascomycota which produce conidia or asci respectively;
Companion Organisms—the target partner entering into a mutualistic association with the biological agent;
Biological agent—viable culture of cyanobacterial cells of the genera, Spirulina, possessing both photosynthetic and nitrogen fixation, metabolic activity.
Experiments were carried out using the following:
Fungal Contaminants: Hypocreaceae—*Trichoderma viride* Canterbury CTV 1; Trichophyton sp. or Epidernophyton sp.—causal agents of tinea pedis dermatocycosis (athlete's foot) in humans. Treatment of the infection was conducted in situ.

The fungal contaminants are available through the Department of Zoology, University of Canterbury, New Zealand.

Companion Organisms—Basidiomycota: *Pleurotus pulmonarius* Canterbury CPP 1 (Oyster mushroom); or human in vivo.

Biological Agent: *Spirulina platensis* (Earthrise Farms, Mass Culture Facilities, California).

Compound Preparation:

Desiccated *Spirulina platensis* cells were rehydrated in 0.84 w/v sodium bicarbonate (pH 8.5) for approximately 12 hours, preferably under illumination (8–80 Watts/m$^2$).

Optionally, the rehydration solution may further contain 0.04–0.25 w/v sodium sulphide to inhibit bacterial growth.

The culture to be stressed by nutrient diminution or partial desiccation to yield a resting stage.

Freeze drying the compound produced an axenic powder. Alternatively, commercially available desiccated *S. platensis* cells (Earthrise Farms) were utilized.

Secondary Infection of Human Peripheral Epidermal Tissue:

Superficial burns and acne pustules were treated in situ. Indications of microbial infection were the formation of pustules (pimple), peripheral inflammation (rubor) and swelling (tumor) at the site of trauma (acne lesion or burn).

Laboratory Trials:

EXAMPLE 1

Companion Organism Infection

*Pleurotus pulmonarius* tissue samples were cultured on PDA plates at 25° C. When the resultant hyphael lawn occupied approximately two thirds of the surface area of the medium, each replicate was streak or spray inoculated with 2.5% *Trichoderma viride* macerated hyphae and spore suspension and incubated for a period of 5–7 days at 25° C. to establish the contaminant to sporulation. Sporulation of the contaminant was visually indicated by the characteristic green coloration of the conidia. The infected plates were subdivided into a control and test series. Advantageously, the intensity of the chlorophyll green coloration of the agent may be used as an indicator of shelf life of a proprietary preparation.

Treatment with Biological Agent:

The test series was individually surface spray treated with the biological agent (0.1%, 1% and 5% w/v).

Whole Plate Comparison:

The composition of the test and control microbial populations were qualitatively monitored on a daily basis. The contaminant *T. viride* completely covered the surface area of the control replicate plates within 2–5 days whereas the relative abundance of *T. viride* infection in the test series reduced over time in the presence of the biological at all tested concentrations (0.1%, 1%, 5% w/v).

Approximately 24 hours after application of the biological agent, the coloration of the contaminant conidia changed from green to a darker green brown. Within four days, the contaminant conidia had the appearance of a green globular mass and the white hyphae of the *P. pulmonarius* rapidly invaded the green material. After 48 hours of further incubation no trace of the contaminant was visible on the surface of the media and the basidiomycete, *P. pulmonarius* recovered completely to form a continuous lawn on the surface of each test plate.

Light and Scanning Electron Microscopy

Comparative morphological observations of *T. viride*-contaminated *P. pulmonarius* cultures were made before and after treatment with the biological agent. Prior to treatment, the branching pattern of the *T. viride* conidiophores was evident, with the phialides differentiating in the characteristic branching structure, terminating in chains of conidia. At one day after treatment the conidia had the appearance of globular structures having little or no surface ornamentation. At day five, the hyphae and conidial structures had coalesced into an amorphous protoplasmic mass which appeared to be unbounded by cell wall. *P. pulmonarius* hyphae were observed to be invading the mass. It was concluded that the contaminant was being saprophytically metabolised by the companion organism, *P. pulmonarius*.

The control series replicates incubated in the presence or absence of light did not form the characteristic 'barking' senescent hyphael mat around the periphery of the growth substrate. The intensity and distribution of the green coloration of the *T. viride* conidia indicated that the contaminant became dominant or out-competed the basidiomycete within a period of 2–3 days from the date of transference of the first control set to the dark growth room. Investigation of the growth substrate found no actively metabolizing *P. Pulmonarius* hyphae. The growth substrate of the control series replicates lost the stability of the block structure as the basidiomycete hyphae decayed.

The test series replicates incubated in the presence or absence of light showed a marked decrease in the relative abundance of the contaminant over time. The cessation of the *T. viride* sporulation occurred within 4–5 days of treatment. However, the test set incubated in darkness was slower to show clearance of the contaminant hyphae from growth substrate (approximately 2–4 days time lag in comparison to that of the test replicates incubated in the light). The characteristic chlorophyll green coloration of the agent was visible on the blocks and fruiting body production occurred.

The experimental procedure was repeated with the basidiomycete, *L. edodes* and the same sequence of events described above was observed.

EXAMPLE 2

Treatment of Contaminant 2.5% *T. viride* macerated hyphae and spore suspension was streak inoculated on PDA plates and incubated for a period of 5–7 days at 25° C. Upon sporulation, each replicate plate was sprayed with 1% w/v of the biological agent over 100% or 50% of the medium surface. Replicates which received 100% spray treatment coverage appeared black within three days of application. The conidiophores and conidia of *T. viride* became desiccated. No viable spores were produced and no regrowth of the contaminant occurred.

Replicates which received 50% spray treatment coverage showed a discrete boundary differentiation between the area which had and had not been sprayed. The area which had been sprayed deteriorated and turned dark brown or black as observed in the replicates which received 100% spray coverage. However, after a period of approximately five days, the boundary gradually broke down and the biological agent migrated into the unsprayed area and attacked the previously undamaged contaminant hyphae. The aforesaid observation demonstrated that the biological agent, like other cyanobacteria, has the ability to move. Cyanobacterial rate of movement has been estimated to be approximately 2.5 mm per day.

EXAMPLE 3

In Situ Treatment of Contaminants

A) Tinea Pedis Infections

Tinea pedis infections cause scaly, annular skin lesions (more commonly known as athlete's foot). In vertebrates, the infection is prominent in the parts of the foot such as between the toes and on the planar surface of the foot. Tinea pedis is a dermatocycotic fungal infection caused by members of the genera Trichophyton or Epidermophyton. The organisms are transmitted by direct contact or by contact with epidermal scales. Fine hyphal threads penetrate the vertebrate dermis and metabolise the host's nutritionally rich fluids. When the fungus is active, the subject experiences intense itching and the skin turns red and cracks. If the infection is left untreated, secondary infections are likely to result. Fifteen human subjects suffering from tinea pedis were instructed to treat their infections by topical application of a cream comprising 25% w/w S. platensis powder in a commercial greasy ointment base. Each subject was given specific instructions to wash the area before application and to apply the cream sparingly on a daily basis to avoid creating a moist barrier that could aggravate the condition. The viability of the biological agent and hence shelf life of the cream was indicated by the intensity of the chlorophyll green coloration.

All fifteen human subjects reported cures within seven days of first application with no adverse effects being noted. Clinical examination and superficial culturing of tissue swabs showed no superficial or peripheral sign of the causal agent.

B) Burns

Preliminary investigations of five subjects have found that a surface spray application of 5% w/v of the biological agent rehydrated compound or topical application of 25% w/w powder of the biological agent dispensed in either a greasy or non-greasy cream reduces peripheral rubor of minor superficial burns. Further, in situ experiments whereby a superficial burn exhibiting tumor and minor infection (i.e. presence of pus) have shown that topical application of the biological agent carried in a cream assisted in the drying out of the pus and reduced healing time. Treatment of burns with the biological agent diminished the incidence of scarring of the new skin forming adjacent the area of epidermal trauma.

C) Acne

Twenty human subjects suffering from acne vulgaris pustules and lesions (pimples), many of whom exhibited acne hypertrophica, were instructed to apply a thin smear of 25% w/w of the biological agent as a powder suspended in a commercially available greasy base at four-hourly intervals during their waking hours.

A dramatic reduction in rubor and tumor was noticeable within twenty-four hours of treatment in all but one subject. In the other nineteen cases, the lesion dried and the pus gradually disappeared to leave a dry, normally pigmented epidermis or a slightly excavate pit in subjects who had exhibited acne hypertrophica.

In subjects presenting minor epidermal infections, the skin appeared normal within 48 hours of treatment. The experimental results were consistent in respect of both irrupted lesions and non-irrupted pustules.

While the invention has been described in respect of a biological control method relating to wounds or traumas of the peripheral epidermis of humans and other mammals, it will be appreciated that the invention could be topically applied to epidermal lesions in a base (i.e. liquid, gel or cream), or impregnated on a surgical dressing to treat or prevent microbial infection, respectively.

EXAMPLE 4

In Situ Treatment of Contaminants

Varicella Infections (Chicken Pox, Water Pox)

Such infections cause erupting papules, vesicles and then pustules. The infection can occur on all parts of the body of the infected mammal. The cause is a *varicella-zoster* virus.

Five human subjects suffering from chicken pox, both pre- and post- vesicle formation, were instructed to treat the affected areas by topical application of a cream comprising 25% v/v powder of the biological agent in a commercial ointment base.

Where vesicles had formed, the subjects treated these with the cream up to four times daily. Subjects with less overt symptoms treated these sites less frequently, to a minimum of a once daily application. Treatment continued at the minimum level for five to seven days after the disappearance of the overt symptoms of the virus.

Subjects noted the cessation of itchiness, sometimes within 30 minutes of application of the cream. Any pustules dried out and any zones of rubor present disappeared within two to five days of initial application. Inflammation also reduced and disappeared within two to five days of the initiation of application. Treatment of the affected areas was continued and subjects noted the lack of formation of scar tissue and the replacement of the wound by normal skin tissue.

Viral Cold Sores

Cold sores of various natures were treated, including herpes virus, herpes simplex. Preliminary investigations found that a thin application of a cream containing 25% v/v powder of the biological agent suspended in a commercially available greasy base was effective.

Seven subjects with varying degrees of severity of the virus were treated. Examples of the viruses treated included chronic sores and sites with secondary microbial infections. The subjects with severe symptoms treated the affected sites with the cream up to four times daily. Subjects with less overt symptoms applied the cream less frequently, to a minimum of a daily application. Treatment continued at the minimum level for five to seven days after the disappearance of the overt symptoms of the virus.

Severe wounds disappeared within two to five days of the beginning of treatment. Fever blisters, stomatitis and associated signs also disappeared within two to five days and each wound was replaced by skin with a new appearance.

EXAMPLE 5

In Situ Skin Repair

A thin application of a cream containing 25% v/v powder of the biological agent suspended in a commercially available greasy base was daily applied by fourteen subjects to face and neck and other areas with affected skin, for a period exceeding two weeks. All subjects had skin defects ranging from the signs of extinct infections, for example old chicken pox scars, to acne and dermatitis. Also present on some but not all subjects were wrinkles, reddened areas and pits.

All subjects noticed a marked reduction in the size of old scarring, a reduction in the areas of redness or affected skin. With constant daily application for a period of longer than two weeks, improvements were noticed by all subjects in some or all of the following areas:

- skin tone;
- skin flexibility increased;
- wrinkles reduced in size, depth or extent (described as smoothing out) or disappeared; and the skin developed an appearance consistent with healthy epidermal cells.

Optionally and additionally the compound could be impregnated on a dressing which is applied externally to a site to treat or prevent infection, respectively. Such dressings are optionally any standard, known dressing which can be stored in sterile manner prior to use.

What is claimed is:

1. A method of preparation of a treated Spirulina compound, said method comprising the steps of:

rehydrating desiccated Spirulina cells in a rehydrating solution for between 1 to 12 hours;

stressing a culture of rehydrated Spirulina cells in said rehydrating solution by one of nutrient diminution or partial desiccation; and subsequently freeze drying the compound.

2. A method of preparation of a treated Spirulina compound as claimed in claim 1 wherein said rehydrating solution contains 0.84 w/v sodium bicarbonate at a pH of 8.5 and the rehydrating is for approximately 12 hours.

3. A method of preparation of a treated Spirulina compound as claimed in claim 1 wherein said freeze drying produces an axenic powder.

4. A method of preparation of a treated Spirulina compound as claimed in claim 3 wherein said compound is further mixed into an aqueous suspension.

5. A method of preparation of a treated Spirulina compound as claimed in claim 3, wherein said compound is further mixed in an admixture which includes a greasy base.

6. A method of preparation of a treated Spirulina compound as claimed in claim 5, wherein said compound is less than 25% by volume of the admixture.

7. A method of preparation of a treated Spirulina compound preparation as claimed in claim 5, wherein said Spirulina is *Spirulina platensis*.

8. A method of preparation of a treated Spirulina compound as claimed in claim 1 wherein said rehydrating is conducted under illumination at between 8 to 80 Watts/m$^2$.

9. A method of preparation of a treated Spirulina compound as claimed in claim 1 wherein the rehydrating solution also contains 0.04–0.25 w/v sodium sulphide.

10. A method of preparation of a treated Spirulina compound as claimed in claim 1 wherein said compound is further mixed into an aqueous suspension.

11. A method of preparation of a treated Spirulina compound preparation as claimed in claim 10, wherein said Spirulina is *Spirulina platensis*.

12. A method of preparation of a treated Spirulina compound preparation as claimed in claim 1, wherein said compound is mixed with a cream in an admixture which includes a greasy base, said preparation being less than 25% by volume of the preparation.

13. A method of preparation of a treated Spirulina compound preparation as claimed in claim 1, wherein said Spirulina is *Spirulina platensis*.

14. A method of preparation of a treated Spirulina compound as claimed in claim 1, wherein said compound is further mixed in an admixture which includes a greasy base.

15. A method of preparation of a treated Spirulina compound as claimed in claim 14, wherein said compound is less than 25% by volume of the admixture.

* * * * *